United States Patent [19]
Marlow et al.

[11] Patent Number: 4,907,453
[45] Date of Patent: Mar. 13, 1990

[54] COLLOID ANALYZER

[75] Inventors: Bruce J. Marlow, Carmel; Tonis Oja, Scarsdale; Philip J. Goetz, Katonah, all of N.Y.

[73] Assignee: Pen Kem, Inc., Bedford Hills, N.Y.

[21] Appl. No.: 298,822

[22] Filed: Jan. 18, 1989

Related U.S. Application Data

[63] Continuation of Ser. No. 879,342, Jun. 27, 1986, abandoned.

[51] Int. Cl.⁴ ............................................. G01N 29/00
[52] U.S. Cl. ...................................... 73/584; 73/61 R
[58] Field of Search ................. 73/61 R, 63, 584, 590; 204/400, 405, 183.3, 183.1, 180.1, 1 T

[56] References Cited

U.S. PATENT DOCUMENTS

| | | | |
|---|---|---|---|
| 3,969,433 | 7/1976 | Kose et al. | 525/305 |
| 4,097,153 | 6/1978 | DeRemigis | 204/183.3 |
| 4,210,504 | 7/1980 | Friedel et al. | 204/180.1 |
| 4,239,612 | 12/1980 | Goetz | 204/299 R |
| 4,254,377 | 3/1981 | Findl et al. | 204/1 T |
| 4,328,000 | 5/1982 | Horn et al. | 436/86 |
| 4,497,208 | 2/1985 | Oja et al. | 73/584 |
| 4,552,019 | 11/1985 | Freeman | 73/584 |
| 4,569,739 | 2/1986 | Kinkowski | 204/180.1 |
| 4,602,989 | 7/1986 | Culkin | 204/180.1 |

OTHER PUBLICATIONS

Beck, U., et al., "Measuring Zeta Potential by Ultrasonic Waves", Tappi, vol. 61, pp. 63–65, Sep. 1978.
Debye, P., "A Method for the Determination of the Mass of Electrolytic Ions", Journal of Chemical Physics, vol. 1, p. 13, 1933.
Hunter, R. J., "Zeta Potential in Colloid Science Principles and Applications", Academic Press, pp. 1–3 (1981).

Primary Examiner—John Chapman
Assistant Examiner—Mark A. Spector
Attorney, Agent, or Firm—S. Michael Bender

[57] ABSTRACT

A colloid analyzer is provided employing a relatively low frequency, low power, continuous "acoustic" wave signal propagated in the direction of spaced electrodes mounted adjacent to the side wall of a chamber or vessel containing a colloid sample. The chamber further comprises a series of probes for respectively sensing the pH, temperature, and conductivity of the sample(s) being analyzed. A piezoelectric transmitter generates the acoustic drive signal. The spaced electrodes in conjunction with an electronic signal processing circuit serves as a receiver and generates an output signal relating to the magnitude and polarity of the zeta potential of the particles being "acoustically" excited by the drive signal. A computer responsive to the signal processing circuit's output signals and/or the vessel probes' output signals alternately develop a graphical output relating to zeta potential, and/or one relating to the surface charge density of the analyzed colloid for given levels of titration. Optional apparatus is provided responsive to the output of the signal processing circuit for measuring the degree of flocculation of the colloid sample in the vessel.

16 Claims, 7 Drawing Sheets

COLLOID ANALYZER

This application is a continuation of application Ser. No. 879,342, filed June 27, 1986, now abandoned.

DESCRIPTION

1. Technical Field

The present invention relates generally to a method and means for determining the electro-chemical properties of colloidal systems, and more particularly, to a method and means for determining the zeta potential and surface charge density of colloidal particles suspended or otherwise dispersed in liquid media.

In the field of colloid chemistry, a need has long existed for instrumentation capable of determining the electrokinetic properties of dispersed particles without limitations being imposed by particle size and/or particle concentration. Thus, it would be extremely valuable to be able to measure the zeta potential and surface charge density of concentrated or opaque dispersions, flowing streams, live cellular organisms, photo sensitive materials, and of very large or very small particles, especially if such determinations could be made automatically and rapidly on a single colloid sample, or continuously in on-line applications, and in any event, simultaneously during the various stages of a titration program.

2. Background Art

In the electrophoretic measuring instrument, disclosed in U.S. Pat. No. 4,046,667, migrating particles under the influence of an applied electric field are viewed through the ocular of a microscope. A scanning galvanometer mirror or prism is adjusted to null the apparent viewed movement of the migrating particles, and the mirror drive voltage necessary to bring about this apparently stationary viewed particle condition together with the electric field strength are used to calculate the zeta potential or electrophoretic mobility of the viewed particles. With this device however, the liquid suspension must be dilute in particle concentration to avoid multiple image scattering, and very large or small particles cannot be analyzed.

An improved, automated electrophoretic measuring device employing optical scanning techniques, is described in U.S. Pat. No. 4,154,669. In this patented instrument, colloidal particles migrating under an applied reversing electric field are optically imaged onto a rotating grating. If the image of a given particle moves in the same direction as the grating, it crosses fewer line pairs per unit time. Thus the signal for that particle will be at a lower frequency than the signal from a reference detector which senses the movement of the grating alone. Conversely, if the image moves in the opposite direction, the signal will be at a slightly higher frequency compared to the reference. Typically, many particles are measured simultaneously, each particle contributing a signal component at a frequency shift determined by its electrophoretic velocity. A frequency analyzer computes a frequency spectrum from this doppler signal and then averages successive spectra to obtain the electrophoretic distribution function.

The rotating grating instrument disclosed in the '669 patent is a significant improvement over the semiautomatic device of the '667 patent because it yields an electrophoretic mobility distribution measurement relatively rapidly and automatically on a single colloid sample. Nonetheless, owing to its dependence upon optical techniques, its use is still limited to dilute suspensions and relatively large or small particles cannot be measured.

U.S. Pat. No. 4,497,208, discloses an instrument which applies a high frequency, high power, electrical pulse train across a pair of electrodes immersed in a vessel containing a colloidal suspension. The pressure amplitude of the resulting pulse train is then sensed with an "acoustic" transducer to derive a signal related in some manner to the zeta potential of the particles being analyzed. Not only is the specific relationship between the derived signal and the actual zeta potential of the measured colloids non-disclosed, but further, the device disclosed in this patent lacks the capability of determining the polarity of the net charge on the particles being analyzed independent of particle concentration and temperature of the suspension medium. Moreover, because this prior instrument depends upon a high power, high frequency pulse train, it is incapable of accurately measuring high conductivity colloids. Finally, the accuracy of the foregoing instrument is limited due to attenuation by the colloid of the high frequency drive signal.

DISCLOSURE OF INVENTION

In accordance with the present invention, a colloid analyzer is provided employing a relatively low frequency, low power, continuous "acoustic" wave signal propagated in the direction of spaced electrodes mounted adjacent to the side wall of a chamber or vessel containing a colloid sample. The chamber further comprises a series of probes for respectively sensing the pH, temperature, and conductivity of the sample(s) being analyzed. A piezoelectric transmitter generates the acoustic drive signal The spaced electrodes in conjunction with a novel electronic signal processing circuit serves as a receiver and generates an output signal relating to the magnitude and polarity of the zeta potential of the particles being "acoustically" excited by the drive signal. Computer means responsive to the signal processing circuit's output signals and/or the vessel probes' output signals alternately develop a graphical output relating to zeta potential, and/or one relating to the surface charge density of the analyzed colloid for given levels of titration. Optional means are provided responsive to the output of the signal processing circuit for measuring the degree of flocculation of the colloid sample in the vessel.

BRIEF DESCRIPTION OF DRAWINGS

The details of the present invention will now be described in connection with the accompanying drawings, in which.

BEST MODE FOR CARRYING OUT THE INVENTION

Before proceeding further, it might be helpful to review briefly the theoretical considerations relating to the present invention. Those skilled in the field of colloid chemistry will appreciate that various electrokinetic phenomena result when a charged interface is moved relative to the continuous phase. In the context of colloids, the charged interface refers to the particle or particle envelope whereas the continuous phase refers to the bulk suspending medium. Four classical electrokinetic techniques have been described in the literature, namely, (i) electrophoresis, the movement of charged colloidal particles under the application of an applied electric field, (ii) electroosmosis, the motion of a liquid in contact with a mechanically restricted charged interface under the influence of an applied electric field, (iii) streaming potential, inducement of an electric field when the continuous phase is caused to move mechanically relative to a mechanically restricted charged interface, and (iv) sedimentation potential or Dorn effect, the inducement of an electric field when charged colloidal particles are caused to move relative to the continuous phase by the mechanical force of gravity.

When charged particles are acted on by an applied electric field, electrophoretic motion results in the direction of the electrode of opposite polarity of the zeta potential of the particle. The velocity of the particles is proportional to the applied electric field, whereas the ratio of the particle velocity to the applied electric field is defined as the electrophoretic mobility U measured in $m^2/Vs$. In accordance with theory developed by Smoluchowski, Huckel, and Henry (1) the mobility, in turn, is related to the zeta potential $\zeta$ which is the potential at the "shear plane" of the particle-liquid interface expressed as $$U = K\zeta \qquad [1]$$

where K is a constant for a particular colloid, e.g., $K = 7.82 \times 10^{-7}$ $m^2/V^2s$ for water at 25 degrees centigrade. Thus, electrophoretic mobility measurements allow determination of the zeta potential which directly correlates with the stability of a charged stabilized colloid, i.e., the resistance of the colloid particles to flocculation. Although the zeta potential correlates directly with stability, it is only an indirect measure of the surface charge sign and magnitude.

In electroosmosis and streaming potential, the measured signals are also proportional to the zeta potential, but are inversely proportional to conductivity $\lambda_o$, i.e., the measured signals are proportional to $K\zeta/\lambda_o$.

The Dorn effect results when charged colloidal particles are acted on by the acceleration due to gravity. The motion of the particles causes the center of charge density of the ionic atmosphere of counter ions surrounding a charged particle to be displaced relative to the center of charged density of the particle. Separation of charge density causes each particle to act as a dipole or an electric field. The electric field is immeasurably small for a single particle, but in a swarm of particles such as in a colloidal system a macroscopic DC electric field results over two electrodes placed along the length of a sedimentation column containing a sedimenting charged colloidal system. Unlike the other electrokinetic effects described above, the sedimentation potential depends on the number of particles present or concentration; the greater the concentration the greater the number of dipoles the greater the measured electric field. Classical electrokinetic theory shows that the macroscopic electric field is related to the zeta potential through $$E = K\phi g (\rho_2 - \rho_1)\zeta/\lambda_o \qquad [2]$$

where $\phi$ is the volume fraction of particles, g the acceleration due to gravity, and $(\rho_2 - \rho_1)$ the difference between particle and liquid density, respectively. Thus, when the particle and liquid density are equal, sedimentation, and hence, the sedimentation potential, vanish.

The above theory for the Dorn effect is valid only in dilute systems (volume fraction < 1%). When the particle concentration increases particle-particle electrical and hydrodynamic interactions occur, and a particle interaction parameter $F(ka,\phi)$ must be included in the expression, i.e., $$E = K\phi g (\rho_2 - \rho_1)\zeta F(ka,\phi)/\lambda_o \qquad [3]$$

where k is the reciprocal Debye length. The particle interaction parameter can be calculated from the Levine et al cell model theory (2). Verification of the applicability of the cell model theory to the Dorn effect has been established by Marlow and Rowell (3).

In the colloid analyzer of the present invention a sample of charged colloidal particles is caused to move relative to the continuous phase in a direction normal to the gravitational field by an acoustic excitation or drive signal. When the charged colloid is subjected to an impinging sound wave, a displacement of the particle relative to the liquid occurs. Centers of charge density of the charged particle and the compensating ionic atmosphere are displaced from equilibrium in exactly the same way as in the Dorn effect, the only difference being the nature of the accelerating force creating the dipole. Under acoustic excitation the accelerating force is dynamic whereas in the Dorn effect the force is static. Thus, in the acoustic technique of the present invention, the charged colloidal particles act as vibrating dipoles. If a pair of spaced electrodes are placed normal to the propagation direction of the acoustic wave and separated by a phase distance other than an integral multiple of the wavelength, an AC potential termed the colloid vibration potential (CVP) will be received having the same frequency as the acoustic drive signal.

Similar alternating potentials were first predicted by Debye in 1933 for ions in an electrolytic solution and termed the ion vibration potential (IVP) (4). Later experiments by others verified Debye's predicted results of IVP theory using pulsed acoustic (5) as well as standing wave techniques (6). Rutgers and Hermans predicted behavior similar to the Debye effect for colloids (7-10) and presented the early theoretical framework to describe the effect. Later theoretical treatments of the acoustic effect in colloids were presented by Enderby (11) and Booth and Enderby (12).

The literature however, fails to verify quantitatively the theoretical predictions of CVP although, some experimental data is available reporting work with pulsed acoustics (13-16).

In accordance with the present invention, it is hypothesized that the colloid vibration potential (CVP) gradient is related to zeta potential in exactly the same way the sedimentation potential field strength is proportional to zeta potential (see equation [2]), the only difference being the accelerating force resulting from the acoustic drive signal, i.e., $$E = CVP/(\lambda/2) = K\phi g_a(\rho_2 - \rho_1)\zeta\lambda_o \quad [4]$$

where $\lambda$ is the acoustic wavelength and $g_a$ the acoustic acceleration. It is to be noted that everywhere in this specification, $\lambda$, the acoustic drive signal wavelength, is to be distinguished from $\lambda_o$, the conductivity of the bulk suspending medium. The acoustic acceleration is given as $$g_a = 2P/\rho_1 (\lambda/2) \quad [5]$$

where P is the pressure amplitude of the acoustic wave Thus, the CVP reduces to $$CVP = K\phi 2P\Delta\rho\zeta/\lambda_o \quad [6]$$

where $\Delta\rho$ is the density of the particles relative to the bulk medium. This is exactly the same expression obtained by Enderby and Booth for their rigorous treatment of a charged colloid particle in an acoustic field (11,12).

Normalizing the CVP for conductivity and pressure amplitude gives the relative acoustic mobility RAM $$RAM = CVP\lambda_2/2P = \phi\Delta\rho K\zeta \quad [7]$$

which has the same units as electrophoretic mobility (m²/vs). It is an important feature of the present invention to determine CVP, conductivity, and pressure amplitude and then combine these quantities to yield the RAM in accordance with equation [7] for a given colloid sample at a given titration level. From equation [7] it is apparent that the calculation of RAM depends on particle concentration and relative particle density. Since these parameters are known or readily obtainable for a given colloidal system, RAM may be normalized to yield the absolute acoustic mobility AM as follows $$AM = RAM/\phi\Delta\rho = K\zeta \quad [8]$$

It is thus seen that a measurement of the absolute acoustic mobility (AM) will lead to a quantity identical to electrophoretic mobility, but with the advantage that such measurement may be made employing the acoustic technique of the present invention for particles ranging in size from ions to aggregates.

Moreover, as in the Dorn effect particle-particle electrical and hydrodynamic interactions occur as the particle concentration increases. This is accounted for in the acoustic technique of the present invention in exactly the same way as in the Dorn effect, i.e. by introduction of the particle interaction parameter $F(ka,\phi)$ $$AM = RAM/\phi\Delta\rho F(ka,\phi) = K\zeta \quad [9]$$

Therefore, since this parameter is readily available for a given colloid system, absolute acoustic mobility measurements may be made at any particle size or concentration as well as on flowing streams, optically opaque and photosensitive colloids, live cellular organisms and so on.

In accordance with the invention, therefore, a colloid analyzer is constructed capable of sensing the colloid vibration potential of an acoustically excited colloid sample and then processing the electrical and other information derived from the sample to solve equations [7], [8] and [9] above and thereby determine the magnitude and polarity of the colloid sample's zeta potential without being limited by particle size or concentration.

Figure 1:
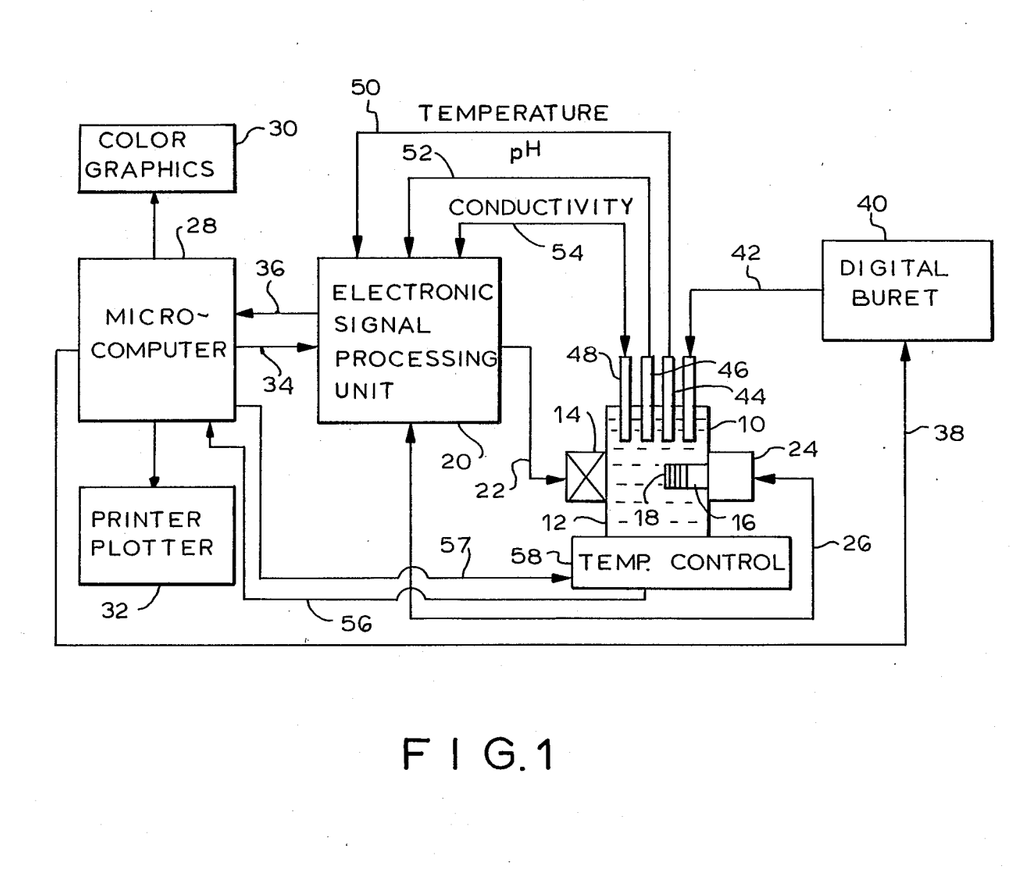
FIG. 1 is a schematic block diagram of the colloid analyzer.

Thus, referring initially to FIG. 1, the general organization of the colloid analyzer of the present invention will now be described. A colloid sample 10 is adapted to be fed or otherwise placed into a vessel or chamber 12 which has mounted in its opposed sidewalls a piezoelectric transducer 14 and a receiver electrode or antenna assembly 16, which latter has coaxially mounted thereon a hydrophone 18. An electronic signal processing circuit 20 to be described in more detail below applies to transducer 14 along line 22 an alternating voltage to cause transducer 14 to generate an acoustic drive signal which in turn, is propagated through colloid sample 10 in an axial direction with respect to antenna 16 and hydrophone 18. Antenna 16 and hydrophone 18 respond to the "acoustically excited" colloid sample 10 in chamber 12 to generate a pair of electrical signals which are amplified in pre-amplifier stage 24 and then fed back to signal processing circuit 20 where they are phase compared to each other and otherwise further processed as will be more fully explained. A general purpose microcomputer 28 having the usual video terminal 30 and output printer 32 is connected to the signal processing unit 20 via an input line 34 and an output line 36 which enables the computer to receive signals from the electronic processing unit. It will be appreciated that the computer 28 has a software program which controls its operation and which sends suitable control signals to the electronic signal processing unit 20 via input line 34. Also by means of the software program contained in computer 28, suitable control signals are applied along line 38 to activate a digital buret 40 for titrating the sample colloid 10 in chamber 12 i.e., admitting precise quantities of chemicals to chamber 12 for admixture with colloid sample 10 via chamber input line 42. A series of sensors or probes 44, 46, 48 are mounted on the top plate of chamber 12 and extend into the chamber to contact colloid sample 10 for measuring the temperature, pH and conductivity of the sample being analyzed. Each probe transmits an output signal along a respective line 50, 5, 54 to electronic signal processing unit 20, which, in turn, applies these signals to computer 28 along output line 36. Finally, a heating element 58 for precisely regulating the temperature of the sample colloid 10 in camber 12 is provided, controlled from computer 28 via lines 56 and 57.

Figure 2:
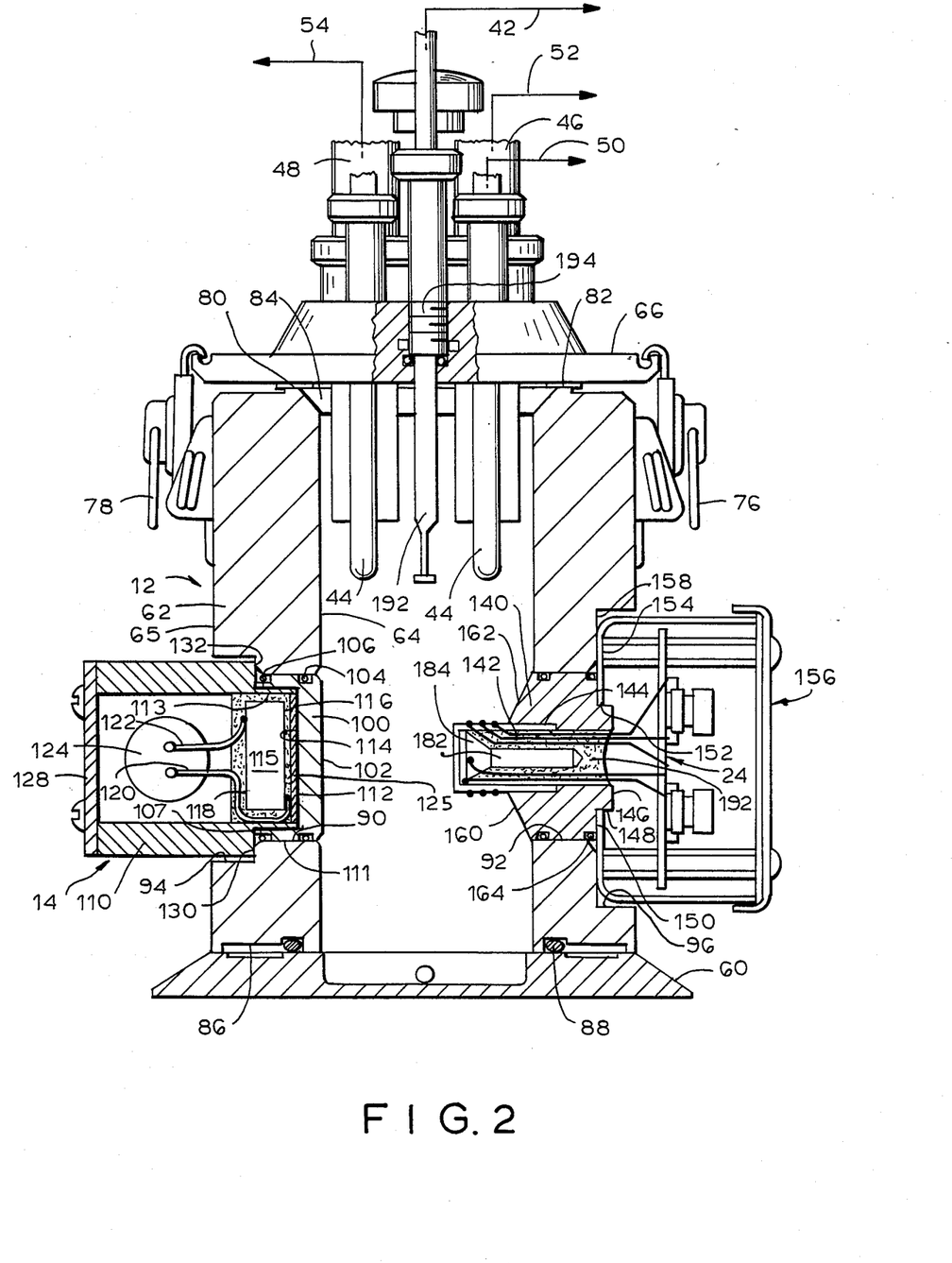
FIG. 2 is a front elevational view in vertical cross-section of the colloid analyzer chamber.
Figure 2A:
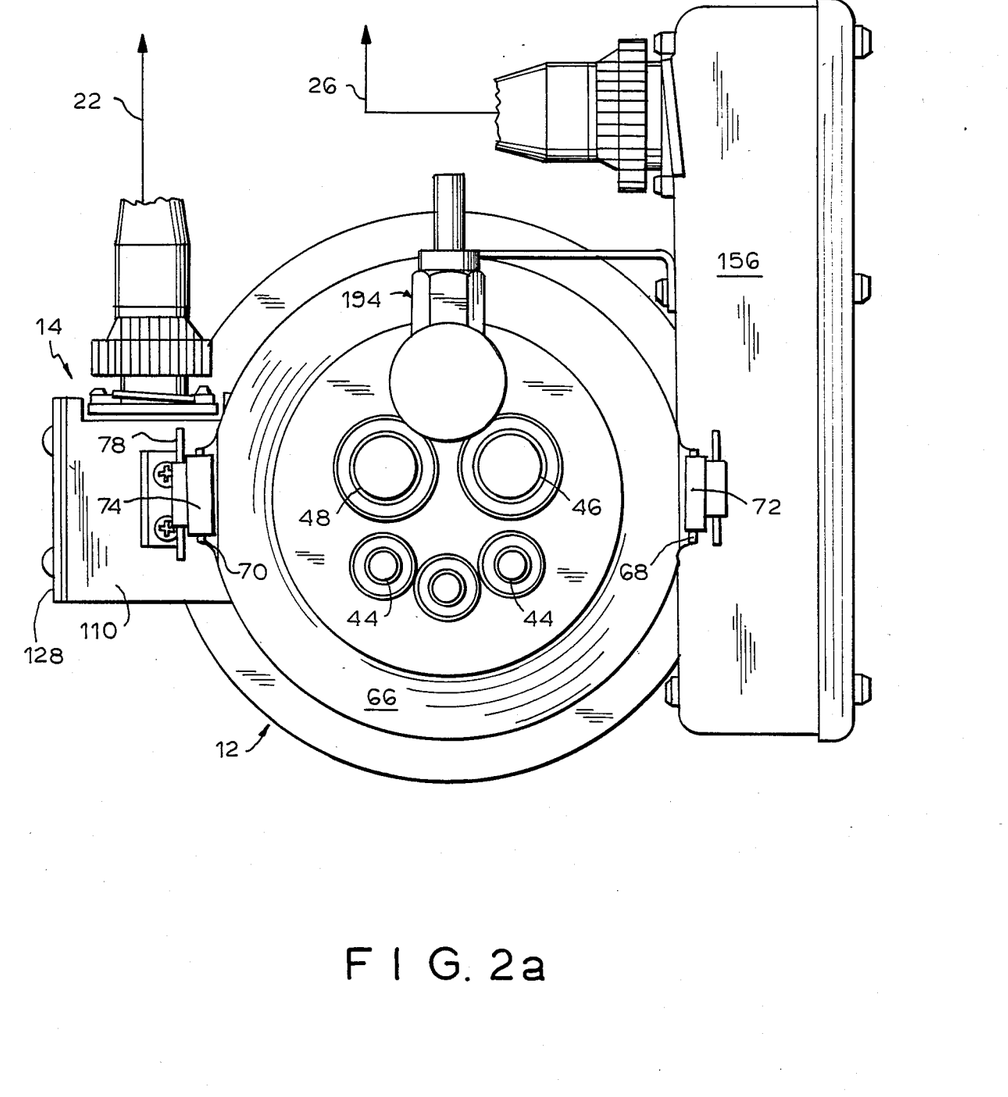
FIG. 2a is a top view of the colloid analyzer chamber of FIG. 2.

Turning now to FIGS. 2 and 2a, chamber 12 comprises a baseplate 60, a generally hollow cylindrically shaped wall member 62 having a central opening 64 therein to define the chamber interior volume, and a top plate 66 having a pair of grooved extensions 68, 70 adapted to be cooperatively engaged by a corresponding pair of conventional clamp assemblies 72, 74 by manual actuation of depressible clamp handles 76, 78. Clamp assemblies 72, 74 are suitably fastened to the outer surface of wall member 62 by screw fasteners or the like. A gasket 80 attached to the confronting under surface of plate 66 engages an annular lip 82 circumferentially surrounding the mouth of the chamber interior formed by beveled surface 84 to form a tight seal of the chamber interior when the clamp assemblies are engaged as shown.

Baseplate 60 is fastened to body member 62 by a series of spaced threaded screw fasteners (not shown) extending into annular end 86 and sealed via annular O-ring 88. The material of baseplate 60 preferably is stainless steel to facilitate the transfer of heat into the interior volume of chamber 12 by means of heating element 58 (FIG. 1). Similarly, top plate 66 also is fabricated of stainless steel. The cylindrical body member 62, on the other hand, also must be fabricated of a durable, chemically inert, dimensionally stable material, but which has the additional property of being highly acoustically absorbent. Polytetrafluroethylene such as sold under the trademark TEFLON is suitable for this purpose and is particularly preferred.

Cylindrical body member 62 has a pair of opposed cylindrical openings or ports 90, 92, coaxially aligned with respect to each other and whose common axis intersects and is generally normal or perpendicular to the central vertical axis of body member 62. Port 90 extends from inner surface 64 partially through the wall of body member 62 whereupon it opens into an enlarged, coaxial cylindrical opening 94 which, in turn, opens into the outer surface 65 of body member 62. Likewise, port 92 extends from inner surface 64 partially through the wall of member 62 whereupon it opens into an enlarged coaxial cylindrical opening 96 communicating with outer surface 65.

Acoustic transducer 14 is interfitted in openings 92, 94 substantially as shown in FIG. 2 and secured to the outer surface of body member 62 by way of a pair of brackets and screw fasteners (not shown). The outer casing of transducer 14 comprises a cylindrical nose portion 100, preferably fabricated of an acrylic resinous material such as, for example, the polymer sold under the trademark POLY 76. Nose portion 100 has a flat outer face 102 at one end thereof positioned generally normal to the axis of opening 90 and flush with inner surface 64 and is sealingly interfitted within recess 90 via a pair of spaced annular O-rings 104, 106 seated in corresponding grooves in the outer cylindrical surface 111 of nose portion 100. The nose portion's open end 107 is fitted over the rim 113 of an enlarged cylindrically shaped stainless steel housing 110 and fastened thereto in a secure manner preferably by means of a thin layer 112 of conductive epoxy adhesive extending entirely across the flat rear surface 114 of front face 102 of nose portion 100, and between rim 113 and the inner surface of the nose portion's sidewall. A piezoelectric transducer element 115 in the shape of a cylindrical disk is coaxially positioned interiorly of nose portion 100 adjacent to conductive layer 112, but spaced slightly therefrom. A pair of thin films or layers 116, 118 of conductive material is adhesively attached or otherwise secured to the front and rear face respectively of transducer element 115. Similarly, a pair of conductors 120, 122 is attached respectively to each conductive layer 116, 118 of element 115 substantially as shown which conductors extend toward and are coupled to an insulated terminal post 124 extending through the wall of steel housing 110 for connection with line 22 (FIG. 1). As is well known, a voltage applied across conductors 120, 122, and therefore, across the conductive films 116, 118 attached to the opposed faces of piezoelectric transducer element 115 will cause the transducer element to vibrate in accordance with the applied voltage. A suitable material for element 115 is lead zirconate titanate and is readily commercially available. The vibrations, in turn, will be transmitted through the front face of nose portion 100 in a direction parallel to the central axis of openings 92, 94 to acoustically excite the colloid sample 10 in chamber 12.

In order to insulate the front conductive surface 116 of transducer 115 with respect to conductive layer 112, a thin insulating layer 124 of Mylar plastic material or the like is disposed between conductive layer 116 and layer 112 of conductive epoxy resin. A conventional potting compound, preferably non-conductive epoxy resin, is employed to fill the space surrounding element 115 to maintain the foregoing parts securely in place, and to facilitate acoustic resonance by the entire transducer unit 115 over a narrow pass band. The rear end of transducer 14 is sealed by a flat stainless steel backing plate 128 using conventional screw fasteners engaging housing 110. It will be appreciated that since the conductive epoxy layer 112 contacts rim 108 of housing 110 a "Faraday cage" or electromagnetic shield completely surrounds transducer element 115.

Also, it will be observed that the annular shoulder 130 formed at the juncture of openings 90 and 94 intermediate the transverse extent of the wall of body member 62 serves as an abutment for the corresponding annular enlargement or shoulder 132 formed on transducer 14 at the juncture of housing 110 and nose portion 100. Thus, transducer 14 may be interfitted with the wall of member 62 by inserting the nose portion of transducer 14 into and through opening 90 until shoulder 132 engages shoulder 130 at which point flat face 102 of the transducer will automatically be aligned with the chamber's inner surface 64 substantially as shown in FIG. 2.

Whereas the surface of front face 102 of nose portion 100 of transducer 14 lies essentially flush with the inner surface 64 of cylindrical wall member 62, the coaxially arranged electrode antenna 16 and hydrophone 18 subassembly projects toward transducer 14 along a direction defined by their common central axis (i.e., the central axis of ports 90 and 92). Electrode antenna 16 thus comprises an elongated, hollow cylindrical support member 134, also preferably fabricated of POLY 76 acrylic resin, closed at its proximal or free end by a flat face portion 136 of substantially smaller outside diameter than the co-axially aligned, confronting spaced 134 nose portion of transducer 14. The cylindrical support member extends rearwardly toward an opposed, open, distal end 138 which is adhesively secured within a corresponding sized central recess 142 provided in a plug member 140 which in turn, is suitably sized for interfittment within opening 92 in the wall of body member 62. The central recess 142 of plug member 140 is reduced in diameter intermedially of the transverse extent of the wall of body member 62 to provide a shoulder 144 against which distal end 138 of support member 134 abutts when the latter is secured to the plug member. The reduced size opening of recess 142 communicates with and forms an extension of the hollow interior of support member 134 which extended recess opens into the surface 146 of a boss 148 projecting from the rear surface 150 of plug member 140. Boss 148 is tightly received through an opening 152 in rear wall 154 of a rectangularly shaped housing generally indicated by reference number 156, preferably fabricated from aluminum material, in which pre-amplifier circuit board 24 is mounted. A series of screw threaded fasteners or the like are employed to connect the rear wall of 154 housing 156 to plug member 140 such that the entire sub-assembly may be interfitted within ports 92 and 96 in the wall of body member 62 by inserting the plug member into recess 92 and then attaching pre-amplifier housing 156 to the outer surface 65 of the body member 62 by means of a bracket (FIG. 2a) and suitable screw threaded fasteners. When so interfitted, rear wall 154 of housing 156 bears against annular surface 158 formed by enlarged port 96 to automatically locate the inwardly facing frustoconically shaped or concave surface 160 of plug 140 substantially as shown in FIG. 2. A pair of spaced O-rings 162, 164 seated in suitable grooves in the circumferential outer surface 166 of plug member 140 prevents leakage through port 92 when the plug 140 is emplaced as shown.

It will be noted that the reason surface 160 of plug member 140 facing into the interior of chamber 12 is frustoconically shaped or concave relative to inner surface 64 is to reduce or minimize standing acoustic waves in the vicinity of the axially extending cylindrical support member 134 whose flat front face 136 extends well beyond the inner surface 64 of the body member.

Figure 3:
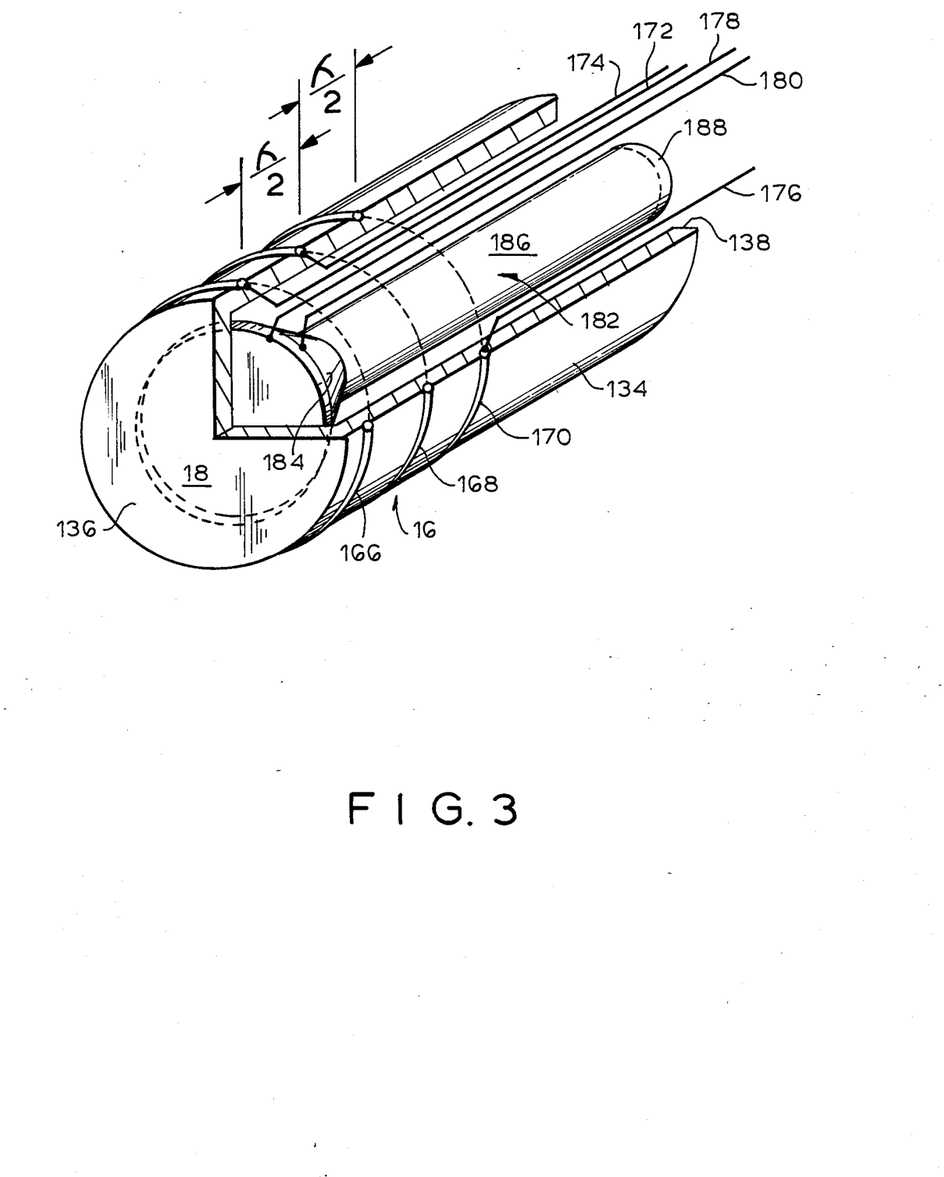
FIG. 3 is a perspective view of a portion of the antenna electrode.

As more clearly shown in FIG. 3 there is provided on the outer cylindrical surface of support member 134 adjacent front face 136, a series of three conductive rings 166, 168, 170 each of which is axially or longitudinally spaced from the other a distance equal to λ2 where λ is equal to the wavelength of the acoustic drive signal produced by transducer 14 in water at 25 degrees centigrade. Each electrode is formed of a single turn or closed loop of platinum wire and is connected via a corresponding throughhole (not shown) in the wall of cylindrical support member 134 to a conductor extending along the inside surface of cylindrical support member 134 and parallel to the support member's central longitudinal axis. Thus, conductive ring 166 completely encircles cylindrical support member 134 on the outside surface thereof and is connected to a conductor 172 which extends within the interior of support member 136 to and through the open end of the cylindrical support member, thence through the extended central recess 142 of plug 140 until finally it is connected to pre-amplifier circuit board 24 in housing 156. Spaced conductive rings 168 and 170 are similarly arranged relative to cylindrical support member 134 and are connected to corresponding conductors 174 and 176 substantially as shown in FIG. 3, which conductors also are connected to pre-amplifier 24 after passing through the extended recess 142 in plug 140. It will be appreciated that when the cylindrical support member 134 and plug member are mounted in the wall of body member 62 as described above, each conductive ring 166, 168, 170 will lie in a plane normal to the central axis of support member 134 and therefore be normal to the propagation direction of the acoustic excitation signal emitted by transducer 14. Thus, as mentioned above, and in accordance with an important feature of the invention, spaced conductive rings 166, 168, 170 are capable of sensing the colloid potential voltage of the acoustically excited colloid sample 10 in chamber 12 and generating an alternating electric voltage signal proportional thereto along conductor paths 172, 174, and 176, respectively.

In accordance with yet another important feature of the invention, hydrophone 18 is positioned interiorly of cylindrical support member 134 proximal to the inner surface of flat front face 136 and comprises a thin film of piezoelectric material preferably of polyvinylidene fluoride such as sold under the trademark KYNAR, and has a pair of metallized layers deposited respectively entirely across the front and rear surface thereof, respectively attached to each metallized layer on the obverse and reverse surface of hydrophone 18 is a separate conductor 178, 180 both of which extend through the interior of cylindrical support member 134 and extended recess 142 in plug member 140 in similar fashion to conductors 172, 174, 176 and are electrically connected to the circuit board of pre-amplifier 24 in housing 156.

To provide dimensional stability for the thin film comprising hydrophone 18, a post member generally indicated by reference numeral 182, comprising a frustoconical base section 184, an elongate cylindrical portion 186 connected thereto, and a rounded or spherically shaped terminus 188 connected to cylindrical portion 186, is positioned coaxially inside cylindrical support member 134 with the confronting surface of frustoconical base portion 184 being adhesively attached to the reverse metallized surface of piezoelectric film 18. It will be noted that the end portion 188 of post member 182 terminates at a juncture longitudinally extended beyond end 138 of cylindrical support member 134 as more clearly seen in FIG. 2. By mounting hydrophone 18 on the post member 182, there is provided a suitable means for acoustically absorbing energy impinging upon hydrophone 18 thereby minimizing reflected and standing waves. The post member 182 is securely maintained in its coaxial position interiorly of support member 134 and extended recess 142 via a conventional potting compound such as epoxy resin as indicated at 192 in FIG. 2. By such arrangement, hydrophone 18 is located in a plane normal to the propagation direction of the acoustic excitation signal transmitted by transducer 14 and parallel to the planes of conductor rings 166, 168 and 170.

Hydrophone 18 functions in the reverse manner as transducer 14. That is, the former piezoelectric element responds to acoustic pressure waves and generates an electrical signal proportional to the magnitude thereof. The electrical output of hydrophone 18 is pre-amplified in pre-amplifier 24 and then applied to signal processing circuit 20 (FIG. 1) where it is utilized in a novel manner to be explained in more detail below, together with the electrical signals sensed and generated by electrodes 166, 168, 170, to develop output signals proportional to both the magnitude and sign of the zeta potential of the colloid sample 10 being acoustically excited by transducer 14 in chamber 12.

As mentioned above in connection with FIG. 1, chamber 12 includes a plurality of probes for measuring the physical/chemical properties of the colloid sample. In the preferred embodiment illustrated, a titration nozzle 192 is received in a suitable sleeve sealingly mounted in a recess 194 in top plate 66 and connected through a flexible hose connection to digital buret 40. A suitable buret is marketed by Brinkmann and designated Metrohm Dosimat 665. On either side of titration nozzle 192, is positioned a pair of temperature probes 44 any one of which may be used to furnish a signal on line 50 proportional to the temperature of colloid sample 10 at any given moment. The other temperature probe is a spare and may be used as desired say, for example, in a feedback loop to regulate temperature control 58 in lieu of computer 28. The preferred temperature probes are marketed by Omega Engineering under model no. PR-11-2-100. Positioned behind titration nozzle 192 and temperature probes 44, as viewed in FIGS. 2 and 2a, are pH probe 46 and conductivity probe 48 for applying electrical signals proportional to these properties along conductors 52 and 54 respectively. A suitable pH probe designated the combination electrode probe is marketed by Sensorex. The conductivity probe preferably is of the four-wire type such as that distributed by TBI as model no. 461. The temperature probes, pH probe and conductivity probe are each threadedly received in a suitable corresponding sleeve sealingly mounted in a recess in top plate 66 in the same manner as titration nozzle 192. Finally top plate 66 further includes a one way valve assembly 194 which may be employed to draw a vacuum within the interior of chamber 12.

An important aspect of the present invention is the fact that the acoustic drive signal generated by transducer 14 and propagated through colloid sample 10 in chamber 12 in the direction of electrode antenna 16 and hydrophone 18 is in the low frequency range and is continuously applied during a measurement period. Since the longitudinal or axial spacing between antenna electrodes 166, 168, and 170 is equal to one half the wavelength of the acoustic drive signal in water at twenty five degrees centigrade, for optimal signal processing, the axial separation between the front face 102 of transducer 14 and the front face 136 of electrode support member 134 desirably should be no more than four or five wavelengths. Employing a chamber 12 having a practical internal volume and taking into account other factors such as power consumption, geometry, and attenuation of acoustic drive signal suggests an acoustic drive signal frequency in the range of 100-500 khz. In the embodiment shown, and without limiting the present invention, excellent results have been achieved using a frequency of 200 khz and this frequency is particularly preferred to generate an acoustic drive signal in conjunction with a chamber 12 having the following dimensions:

| | |
|---|---|
| Internal height baseplate to top plate | 125.0 mm |
| Internal diameter | 50.0 mm |
| Diameter of transduce 14 | 25.4 mm |
| Diameter of hydrophone 18 | 12.0 mm |
| Axial separation between transducer front face and hydrophone front face | 30.0 mm |
| Axial distance of hydrophone front face from inside wall surface measured at intersection with port 92 | 20.0 mm |
| Chamber internal volume | 230.0 ml |
| Diameter of conductor rings 166, 168, 170 | 15.0 mm |
| Thickness of each conductor ring | 0.25 mm |
| Axial spacing between conductor rings 166, 168, 170 | 3.75 mm |

In the operation of the colloid analyzer of the present invention, a sample colloid is placed into chamber 12 and top plate 66 clamped in place by actuation of clamp assembly handles 72, 74. Computer 28, which preferably comprises an IBM PC enhanced AT with 30 Mbyte hard disk, but which may comprise any equivalent stand alone programmable micro-computer, in conjunction with a suitable stored program, the details of which are outside the scope of the present invention, may then be used to initiate various control signals to commence a measurement cycle to say, determine the RAM (equation [7]) of the colloid being analyzed. It will be understood that prior to the measurement cycle, and under the automatic control of the computer and software program, appropriated signals have been applied along conductors 34, 38, 57, etc., (FIG. 1) to calibrate probes 44, 46, and 48, initialize digital buret 40 to run a predetermined titration program if one is desired, and so on, all as fully comprehended by those skilled in the art of colloid instrumentation.

Figure 4:
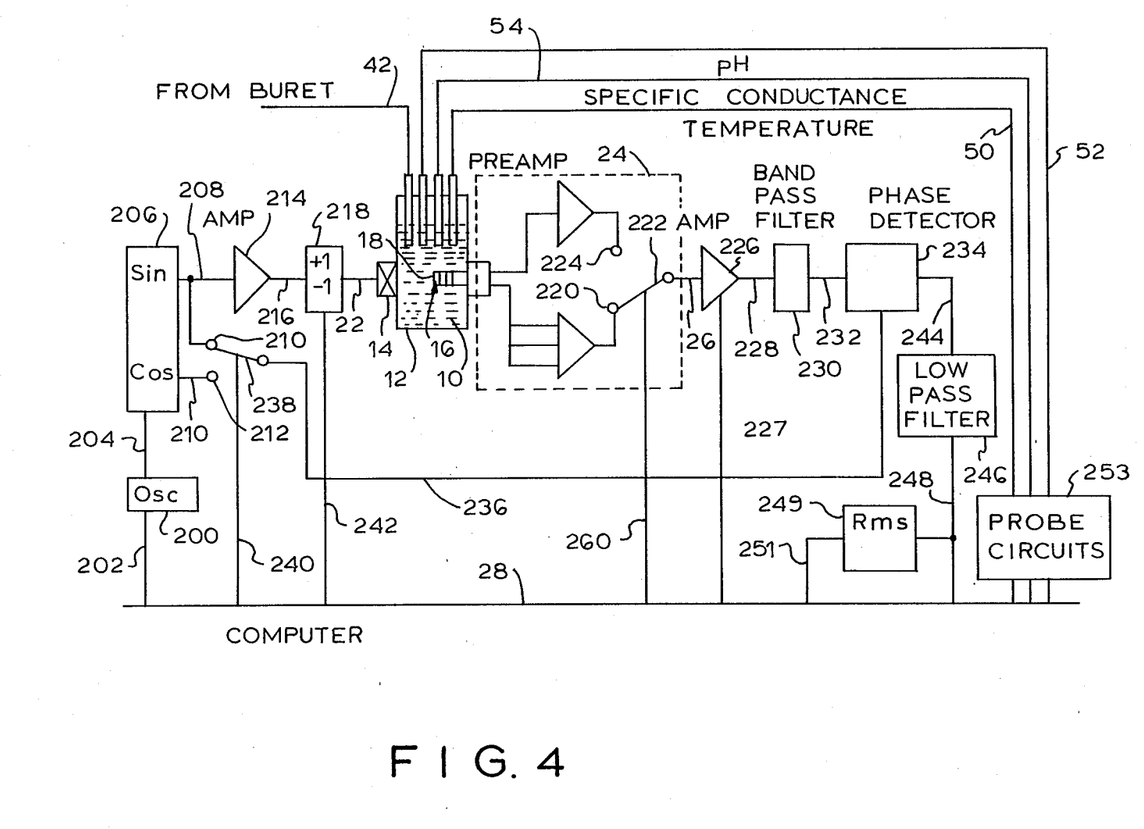
FIG. 4 is a schematic block diagram of the signal processing circuit portion of FIG. 1.

The measurement of RAM essentially is carried out via operation of the electronic signal processing unit 20 under the aegis of computer 28 as will now be explained with reference to FIGS. 4 and 4a. An oscillator 200 activated by a suitable on-off signal received from computer 28 along line 202, generates a sinusoidal voltage having a frequency in the preferred embodiment of 200 khz. The output of oscillator 200 is applied to quadrature reference generator 206 via conductor 204 which functions to apply a pair of output voltages on lines 208 and 210 equal to the sin and cos respectively of the oscillator output signal. The output signal on line 208 is then amplified in amplifier 214, passed through inverter 218 via line 216, and the inverter output is delivered to conductor 22 to drive transducer 14.

As explained previously, transducer 14 responds to the applied input signal on line 22 to generate an acoustic pressure wave in chamber 12 which is propagated through the colloid sample 10 in a direction parallel to the axis of antenna 16 comprising the three spaced electrodes 166, 168, and 170. Each electrode ring senses the colloid vibration potential manifested by the acoustically excited colloid and generates, in turn, an alternating voltage signal, respectively, which is then amplified in pre-amplifier stage 24 as follows. The signals on conductive rings 166 and 168 are fed through a first differential amplifier, whereas the signals on conductors 168 and 170 are fed through a second differential amplifier, and the outputs of the first and second amplifiers are then combined in a third differential amplifier to yield an amplified signal proportional to $$G[-e_1/2 + e_2 - e_3/2] \qquad [10]$$

where G is the overall gain, and $e_1$, $e_2$, and $e_3$ are the potentials sensed by conducting rings 166, 168, and 170, respectively. By this amplifying technique, unwanted spurious signals are rejected from the amplified output signal which latter is then amplified again through a further gain controlled amplifier stage 226 after passing through contact 220 and the armature of single-pole double-throw relay 222 and conductor 26.

The output of amplifier 226 is then passed through band pass filter 230 via line 228 and the filtered signal delivered to phase detector 234 via line 232.

In accordance with still yet another important feature of the present invention, the colloid vibration potential information containing signal on line 232 applied to phase detector 234 is phase compared to a reference signal made available on line 236 and also applied to phase detector 234 from sin/cos generator 206. Hence, the reference signal comprises the quadrature component of the transducer input drive signal generated by oscillator 204, depending upon the position of the armature of relay 238, i.e., the reference signal made available to phase detector 234 on line 236 will either be the sin or the cos component of the oscillator output signal appearing on either contact 210 or contact 212 of relay switch 238. The switching frequency of relay 238 is chosen to permit phase comparison with either the sin or cos component over a period of approximately three seconds whereas the inverted control signal on line 242 has approximately one half the frequency. Therefore, the input signal to transducer 14 appearing on line 22 will be phase shifted 180° approximately every six seconds. This is shown diagrammatically in FIG. 4a where at $t_1$ equal to six seconds, relay 238 has applied both sin and cos components as reference signals sequentially to phase detector 234. As also seen in FIG. 4a, during $t\frac{1}{2}$ equal to three seconds, when the sin component reference signal is being phase compared with the signal on line 232 (represented generally by waveform 238), the output signal of phase detector 234 after being passed through low pass filter 246 via line 244 is rectified and comprises a DC voltage output proportional to A sin$\theta$ where A is equal to the amplitude of the input signal to phase detector 234 on line 232, and 8 is equal to the phase shift between the signal appearing on line 232 and the reference component also being applied to phase detector 234.

At the end of period $t\frac{1}{2}$, when the cos component of the reference signal is being applied to phase detector 246 on line 236 for comparison with the input signal on line 232, the DC output of phase detector 234 and low pass filter 248 is proportional to A cos$\theta$ where again A is the amplitude of the AC input to phase detector via line 232 and $\theta$ is the phase shift of the signal on line 236 relative to the input signal on line 232.

The foregoing process is repeated over the time period $t_1$ to $2t_1$ by merely causing inverter 218 to shift the phase of the transducer drive signal on line 22 by 180 via an appropriate logic signal from computer 28 on line 242. The DC output sin and cos components during the inverted or phase shifted period $t_1$ to $2t_1$ may then be subtracted from the corresponding quadrature signal components obtained during period $t_1$ to produce sin and cos components from which all coherent leakage signals have been cancelled.

Accordingly, after the period $2t_1$ the processed signals, i.e., the stored output of filter 256, may be employed to calculate the amplitude A of the CVP in computer 28 in a conventional manner by solving the following equation $$A = \sqrt{(A\sin\theta)^2 + (A\cos\theta)^2} \quad [11]$$

Similarly, the phase of the phase detector input signal on line 232 may be determined in the computer 22 by solving the following equation
$\theta = \tan^{-1}(\sin\theta/\cos\theta)$ [12]

with due regard being given to the polarity of both A sin$\theta$ and A cos$\theta$.

Figure 4A:
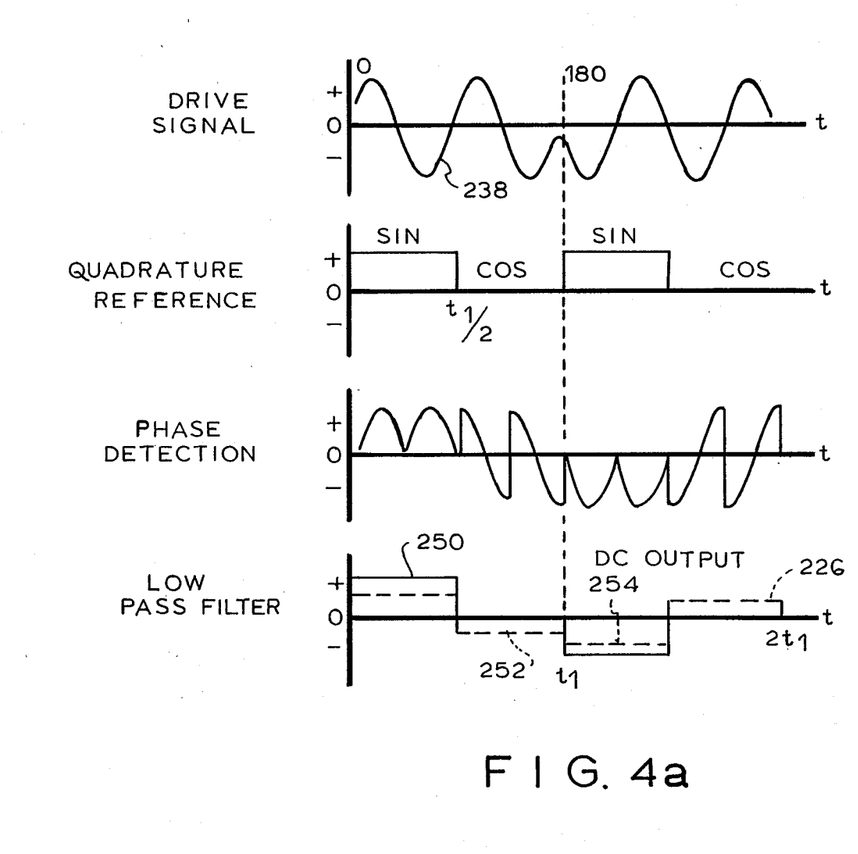
FIG. 4a is diagrammatic graphical plot showing the waveforms of certain signals processed by the circuit of FIG. 4.

With reference to FIG. 4a, it will be appreciated that when there is zero phase shift between the input signal to phase detector 234 and the quadrature reference component on line 236, there will be zero DC output from filter 246 during the period of time when the cos component is being compared. Conversely, during the period of time the sin component is being compared, the DC output of filter 246 will be a maximum. However, this ideal case rarely if ever occurs, and in practice, there will always be some phase shift producing a DC output signed from filter 246 during both sin and cos phase comparisons. This is indicated by the dotted lines 250, 252, 254, and 256 in FIG. 4a.

Although the electrical information obtained in the foregoing manner from the antenna electrode assembly 16 in conjunction with operation of the electronic processing circuit during the period $2t_1$ when the armature of relay 222 engages contact 220, yields the amplitude of the CVP corresponding to the acoustically excited colloid sample 10 in chamber 12 during the same time period, it is not yet possible to determine the polarity of CVP or calculate RAM.

In order to obtain the polarity information unambiguously, i.e., independent of particle concentration or temperature, and calculate RAM in accordance with the present invention, the output of hydrophone 18 must be processed in a manner similar to that of the electrode antenna output signal. This is accomplished by activating relay 222 via an appropriate logic signal furnished by computer 28 along line 260 thereby causing armature of relay 222 to engage contact 224 so that the output of hydrophone 18 after being pre-amplified in pre-amplifier 24 is made available on line 26. When this occurs, the alternating voltage signal on line 26 will be proportional to the pressure amplitude of the acoustic drive signal generated by transducer 14. That signal may then be processed in the same manner as previously described in connection with the antenna electrode 16 output signal, i.e., it is synchronously phase detected relative to the quadrature components of the transducer drive signal over period $t_1$, phase shifted 180° and repeat processed to develop separate pairs of sin and cos components which may be subtracted from each other to obtain sin and cos components of the output signal independent of coherent leakage. The resulting DC output signals representing B sin$\phi$ and B cos$\phi$ respectively, where B is proportional to the pressure amplitude of the acoustic drive signal, the proportionality constant being precalibrated in a known manner, are then processed in computer 28 by solving equations [11] and [12] as above to yield the pressure amplitude and phase of the output of hydrophone 18 as determined over the period $2t_1$ to $4t_1$.

The voltage magnitude output of pre-amplifier 24 may change over a wide range depending upon whether the hydrophone amplifier signal or the antenna electrode signal is applied via relay 222 to line 26. In order to maintain the input voltage to phase detector 234 at a substantially constant, desirable level, the gain of amplifier 226 is regulated by appropriate logic signals made available along line 227 via a suitable algorithm in computer 28. A band pass filter 230 tuned to the acoustic drive frequency (e.g. 200 khz) also is provided to remove unwanted frequency components from the phase detector input. As is well known, the output of the phase detector preferably is passed through a low pass filter 246 to remove noise and to smooth the phase detector D.C. output voltage.

Thus, at the end of a measurement period $4t_1$, or approximately 24 seconds, the necessary information will be stored in computer 28 to determine polarity and magnitude of CVP and pressure amplitude of the acoustic drive signal all of which is required to calculate RAM from equation [9].

With regard to polarity, a reference colloid having a known polarity is analyzed in the colloid analyzer of the present invention in the foregoing manner to produce the phase information from antenna 16 and hydrophone 18. These relative phase angles are then subtracted from each other in computer 28 and set to zero if the polarity of the colloid is positive, or conversely, set to 180 if the polarity of the known colloid is negative. Thereafter, during subsequent measurements of other colloids, the polarity of CVP may easily be determined by comparing the phase difference of the colloid of unknown polarity as measured during the period $4t_1$; with the previously calibrated reference colloid phase information. This novel method of determining the polarity of CVP is independent of temperature and particle concentration because both antenna phase and hydrophone phase angles will change by the same extent when these variables change resulting in no net change in phase difference.

In order to calculate RAM from equation [9], all that is needed therefore, other than the magnitude and polarity of the CVP and the pressure amplitude of the acoustic drive signal (which are obtainable in the manner described above) is knowledge of the colloid's conductivity which easily may be obtained via probe 48. Thus equation [9] may be solved in computer 28 for a measurement period $4t_1$, and the result either displayed on a video output monitor or graphically plotted.

Figure 5:
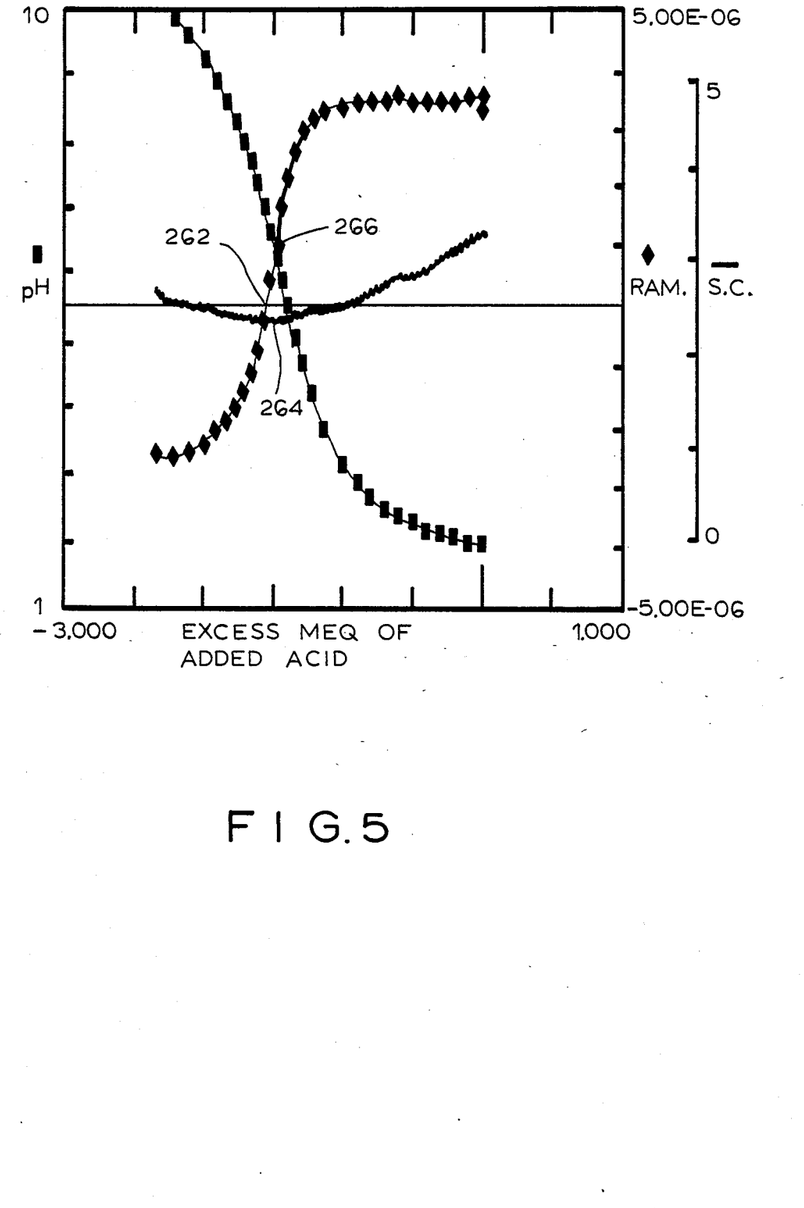
FIG. 5 is a graphical plot representing a typical output of the colloid analyzer.

Typically, RAM will be measured many times in succession during a titration program in which digital buret 40 receives appropriate control signals from computer 28 and adds a precise aliquot of chemical titrant to the colloid sample 10 in chamber 12. As the titration program progresses, each measurement point may be recorded and/or displayed for RAM, pH, and conductivity (s.c.). Thus, FIG. 5 shows a representative graphical recording from computer 28 illustrating the measurement points of a titration program for a typical colloid comprising a 1% by volume titanium dioxide dispersion at pH 2.0 in a supporting electrolyte concentration of 0.01M KCl solution. The particular titration program of FIG. 5 calls for the addition of 1M KOH to the colloid and the graph clearly illustrates the effect of the change in pH versus changes in RAM and specific conductivity, as each of these parameters are calculated during a measurement cycle. It will be noted that the isoelectric point, i.e., the point where RAM is zero, indicated by reference numeral 262 in FIG. 5, is graphically depicted as well as changes in the magnitude and sign of RAM as the colloid is titrated.

Although the RAM is directly proportional to the zeta potential (see equation [8]) the zeta potential is only an indirect measure of the sign and magnitude of the surface charge density. The surface charge density however, can be measured directly by both potentiometric and conductometric titration coincidentally with the measurement of RAM. Thus, when the conductivity of a colloid sample 10 is measured as an appropriate reagent is titrated into the chamber 12, the conductivity as determined by probe 48 will decrease. Once the surface groups have been neutralized, further addition of reagent contributes free electrolyte to the solution and the conductivity begins to increase. The minimum in the conductivity curve versus titration amount gives the equivalence point, or the point where all the surface sites have been neutralized. With reference to FIG. 5, the equivalence point for the colloid undergoing titration is depicted by reference numeral 264. The charge density D which represents equivalents of surface charge groups per unit weight of particles may be obtained from $$D = VC/W \qquad [13]$$

where W(g) is the weight of the colloid particles in chamber 12, C(meq/ml) the concentration of reagent in digital buret 40 and V(ml) the equivalence point (see reference numeral 264 in FIG. 5).

If the diameter d(microns) and density(g/ml) of the particles are known, then the surface charge density s which represents the titratable groups per square angstrom is obtained from $$s = 1.004 D \rho_2 d \qquad [14]$$

and P=1/s is the actual "parking area" or the average area occupied by each titratable group. If several different types of titratable surface groups are present multiple equivalence points will occur on the conductometric titration curve and each group's surface density and strength can be measured.

As mentioned above, another method to measure surface charge density is potentiometric titration which may also be employed using the colloid analyzer of the present invention. In a potentiometric titration, a voltage is measured from an electrode responsive to changes in hydrogen ion concentration (i.e., pH probe 46) for a given titration level. As a potentiometric titration proceeds, an initial buffer region is encountered where the signal from the pH probe varies only slightly with titrant volume i.e., the initial portion of pH titration run curve in FIG. 5. Further addition of titrant causes an abrupt change in pH with titrant volume. The steepest point on the curve or the point where the pH versus titrant volume slope is maximum defines the equivalence point similar to the conductometric titration and is shown in FIG. 5 by reference numeral 266. From this equivalence point the surface charge density is obtained in accordance with equations [13] and [14] as above. As in conductometric titration multiple equivalence points are possible depending on the strength and number of titratable surface group types.

From the foregoing, it will be apparent that the colloid analyzer of the present invention is capable of efficiently measuring zeta potential magnitude and polarity, and surface charge density without being limited to particle size and/or concentration. It is desirable to make both measurements because knowledge of both yields complete information regarding the electrokinetic properties of the colloid being investigated. Those skilled in the art will appreciate that many additional modifications and changes may be made to the present invention. For example, chamber 12 may be provided with input and output passages so that a continuous stream of colloid samples of the same or similar type may be analyzed thus permitting on-line measurements rather than batch analysis. Furthermore, as indicated in FIG. 4, a conventional RMSD (Root Mean Square) meter 249 may be used to sense the fluctuation of the DC output of filter 246 and phase detector 234 made available on line 248 to produce an output signal on line 251 proportional to the degree of flocculation of the sample colloid being analyzed.

Accordingly, it is desired that the present invention be limited only by the true spirit and scope of the appended claims.

REFERENCES CITED

1. R. J. Hunter, "Zeta Potential in Colloid Science", Academic Press, New York, N.Y. p. 69.
2. S. Levine, G. Neale, and J. Epstein, J. Colloid Interface Sci. 57, 424 (1976).
3. B. J. Marlow and R. L. Rowell, Langmuir 1, 83 (1985).
4. P. Debye, J. Chem. Phys. 1, 13 (1933).
5. J. Buogosh, E. Yeager, and F. Hovorka, J. Cham. Phys. 15(8), 542 (1947).
6. R. Zana and E. Yeager, "Ultrasonic Vibration Potentials," Dept. of Chemistry, Case Western Reserve University, Cleveland, Ohio, Tech. Report No. 45, Office of Naval Research, Contract N00014-75-C-0557, Project NR 384-305, Nov. 15 (1978).
7. J. Hermans, Phil. Mag. 25 426 (1938).
8. J. Hermans, Phil. Mag. 26 674 (1938).
9. A. Rutgers, Physica 5, 46 (1938).
10. a. Rutgers, Nature 157, 74 (1946).
11. J. Enderby, Proc. Phys. Soc. 207A, 329 (1951).
12. F. Booth and J. Enderby, Proc. Phys. Soc. 208A, 321 (1952).
13. E. Yeager, J. Bugosh, F. Hovorka, and J. McCarthy, J. Chem. Phys. 17, 411 (1949).
14. E. Yeager, H. Dietrick, and F. Hovorka, J. Acoust. Soc. Am. 25, 456 (1953).
15. E. Yeager, J. Dereska, and F. Hovorka, Tech. Report No. 23, Western Reserve University, Ultrasonic Research Laboratory, Cleveland, Ohio (1960).
16. R. Zana and E. Yeager, J. Phys. Chem. 71, 3502 (1967).
17. U. Beck, R. Zana, and E. Rohloff, TAPPI 61(9), 63 (1978).
18. R. Zana and E. Yeager, U.S. Clearinghouse Fed Sci. Tech. Inform., AD-681063, Case Western Reserve University, Cleveland, Ohio (1980).

We claim:

1. Apparatus for analyzing colloids comprising: a chamber for storing the colloid being analyzed, transducer means adapted to generate a continuous acoustic wave signal at a predetermined frequency for acoustically exciting the colloid stored in the chamber, means for sensing the colloid vibration potential of said acoustically excited colloid in said chamber, and means responsive to said sensing means wherein said sensing means comprises antenna means and hydrophone means responsive to the acoustic excitation generated by said transducer means in said colloid, and said means responsive to said sensing means comprises means responsive to said antenna means, said hydrophone means and said transducer means to generate an output signal related to both the magnitude and polarity of the zeta potential of said acoustically excited colloid, and wherein said means responsive to said sensing means comprises phase comparison means alternatively coupled to the output of said antenna means and said hydrophone means, said phase comparison means also being coupled to means for generating the sin and cos of an electrical reference signal having the same frequency as the acoustic excitation signal generated by said transducer means, wherein the output of said phase comparison means comprises information relating to both the magnitude and polarity of the zeta potential of the acoustically excited colloid.

2. The apparatus of claim 1 wherein phase comparison means further comprises means for periodically inverting the transducer excitation signal to develop an output signal and means for subtracting said phase comparison output signal when said transducer signal has been inverted from said phase comparison output signal when said transducer signal has not been inverted to develop a phase comparison output signal free of leakage error components.

3. The apparatus of claim 1 further comprising means responsive to said phase comparison output for determining the degree of flocculation of said colloid.

4. Apparatus for analyzing colloids comprising: a chamber for storing the colloid being analyzed, transducer means adapted to general a continuous acoustic wave signal at a predetermined frequency for acoustically exciting the colloid stored in the chamber, means for sensing the colloid vibration potential of said acoustically excited colloid in said chamber, and means responsive to said sensing means wherein said sensing means comprises antenna means and hydrophone means responsive to the acoustic excitation generated by said transducer means in said colloid, and said means responsive to said sensing means comprises means responsive to said antenna means, said hydrophone means and said transducer means to generate an output signal related to both the magnitude and polarity of the zeta potential of said acoustically excited colloid, and wherein said hydrophone means is coaxially mounted relative to said antenna means inside said chamber.

5. The apparatus of claim 4 wherein said antenna means comprises at least a pair of conductive rings having a spacing relative to one another relating to the wavelength of said transducer output signal.

6. The apparatus of claim 5 wherein said antenna means comprises at least three spaced conductive rings thereby forming two pairs of rings sharing a common ring, the spacing between said rings in each of said two pairs being related to one half the wavelength of said transducer output signal.

7. The apparatus of claims 5 or 6 wherein said conductive rings are mounted on the outer surface of an elongated hollow support member having a pair of opposed ends, one of said opposed ends of said support member freely extending into said chamber interior in the direction of said transducer, the other of said opposed ends being affixed to the inside wall surface defining said chamber said hydrophone means comprising a piezoelectric element mounted proximal to said one opposed freely extending end of said support member interior thereof, and conductive path means extending from said element towards said other opposed end of said support member.

8. The apparatus of claim 7 wherein said piezoelectric element is mounted of a post member inside said support member, said post member having acoustic absorbent properties.

9. The apparatus of claim 7 wherein said transducer is mounted on said inside wall surface at a location remotely spaced from said wall surface where said other opposed end of said support member is affixed.

10. The apparatus of claim 9 wherein said location of said inside wall surface where said transducer is mounted is spaced from said hydrophone means piezoelectric element by a distance equal to 4 or 5 wavelengths of said transducer output signal.

11. Apparatus for analyzing colloids comprising: a chamber for storing the colloid being analyzed, transducer means adapted to generate a continuous acoustic wave signal at a predetermined frequency for acoustically exciting the colloid stored in the chamber, means for sensing the colloid vibration potential of said acoustically excited colloid in said chamber, and means responsive to said sensing means for generating an output signal related to the zeta potential of said acoustically excited colloid wherein said sensing means comprises three spaced conductor rings supported in said chamber, and said means responsive to said sensing means comprises amplifier means, and wherein the output of said amplifier means is equal to $$G[e_1/2e_2 - e_3/2]$$

wherein, $e_1$, $e_2$ and $e_3$ represent the colloid vibration potential sensed by each conductive ring respectively, and G is equal to the gain of the amplifier.

12. The method for analyzing a colloid comprising the steps of: propagating a continuous wave acoustic excitation signal of predetermined frequency in a colloid, sensing the colloid vibration potential of said acoustically excited colloid, and extracting an output signal from said colloid vibration potential related to the zeta potential of said acoustically excited colloid wherein said extracting step further comprises the steps of: comparing said output signal to the quadrature components of a reference signal related to said predetermined frequency to develop a first pair of sin and cos output signals, converting the pressure amplitude of said acoustic excitation signal into a signal electrical output signal, comparing said second electrical output signal to the quadrature components of said reference signal related to said predetermined frequency to develop a second pair of sin and cos output signals, and combining said first pair of sin and cos output signals with the said second pair of sin and cos output signals to develop output signal related to the magnitude and phase of the zeta potential of said excited colloid and to the magnitude of said pressure amplitude, respectively.

13. The method of claim 12 further comprising the steps of: determining the conductivity of said colloid to produce an output signal relating to the electrophoretic mobility of said colloid, and normalizing said equation for particle concentration and relative particle density.

14. The method of claim 12, further comprising the steps of: simultaneously determining the surface charge density of the acoustically excited colloid.

15. The method of claim 14 wherein said step of simultaneously determining the surface charge density of the acoustically excited colloid comprises the steps of: determining the conductivity and pH of the acoustically excited colloid, repeating the foregoing steps a predetermined number of times during a titration program in which the acoustically excited colloid is combined with successive amounts of an additive to change its properties, generating graphical plots of the change in pH and conductivity resulting from said titration, determining the equivalence point by determining the maximum slope for pH versus additive volume, and the minimum in the conductivity versus additive volume and then solving the equation $$D = VC/W$$

to obtain the equivalents of surface charge per unit weight colloid D where W is the weight of colloid particles being titrated, C the concentration of reagent in the titrant, and V the equivalent point.

16. The method of claim 15 further comprising the step of solving equation $$s = 1.004 D \rho_2 d$$

to obtain the surface charge density s where $\rho_2$ is the density of the colloidal particles and d the particle diameter.

* * * * *